(12) United States Patent
Avery et al.

(10) Patent No.: US 8,951,953 B2
(45) Date of Patent: Feb. 10, 2015

(54) CLEANING FLUID COMPRISING GLYCERIN AND A CULTURE OF MICROORGANISMS

(71) Applicant: My Safe Spray (Holding) Ltd., Reigate (GB)

(72) Inventors: Gillian Susan Avery, East Grinstead (GB); Michael Peter Vernon, East Grinstead (GB); William Michael Crockett, East Grinstead (GB); Laura Dawn McLean, East Grinstead (GB)

(73) Assignee: My Safe Spray (Holding) Ltd., Reigate (GB)

( * ) Notice: Subject to any disclaimer, the term of this patent is extended or adjusted under 35 U.S.C. 154(b) by 0 days.

(21) Appl. No.: 14/359,631

(22) PCT Filed: Nov. 20, 2012

(86) PCT No.: PCT/GB2012/052866
§ 371 (c)(1),
(2) Date: May 21, 2014

(87) PCT Pub. No.: WO2013/076468
PCT Pub. Date: May 30, 2013

(65) Prior Publication Data
US 2014/0342973 A1  Nov. 20, 2014

(30) Foreign Application Priority Data
Nov. 21, 2011 (GB) .................................. 1120014.4

(51) Int. Cl.
*C11D 3/43* (2006.01)
*C11D 3/38* (2006.01)
*C12N 1/20* (2006.01)
*C12N 1/14* (2006.01)
*C12N 1/16* (2006.01)

(52) U.S. Cl.
CPC ........ *C11D 3/381* (2013.01); *C12N 1/20* (2013.01); *C12N 1/14* (2013.01); *C12N 1/16* (2013.01)
USPC ........... 510/195; 510/111; 510/188; 510/194; 510/220

(58) Field of Classification Search
USPC .......................... 510/111, 188, 194, 195, 220
See application file for complete search history.

(56) References Cited

U.S. PATENT DOCUMENTS 7,745,202 B2   6/2010   Higa
2007/0190625 A1*  8/2007   Higa ............................ 435/134

FOREIGN PATENT DOCUMENTS

JP   2003299422 A   10/2003

OTHER PUBLICATIONS

International Search Report and Written Opinion for International Application No. PCT/GB2012/052866, mailed Jan. 24, 2013, 9 pages.

* cited by examiner

*Primary Examiner* — Charles Boyer

(57) ABSTRACT

A cleaning fluid comprising glycerin and a culture of microorganisms, said culture comprising lactic acid bacteria, actinomycetes, photosynthetic bacteria, yeast and fungi.

19 Claims, 1 Drawing Sheet

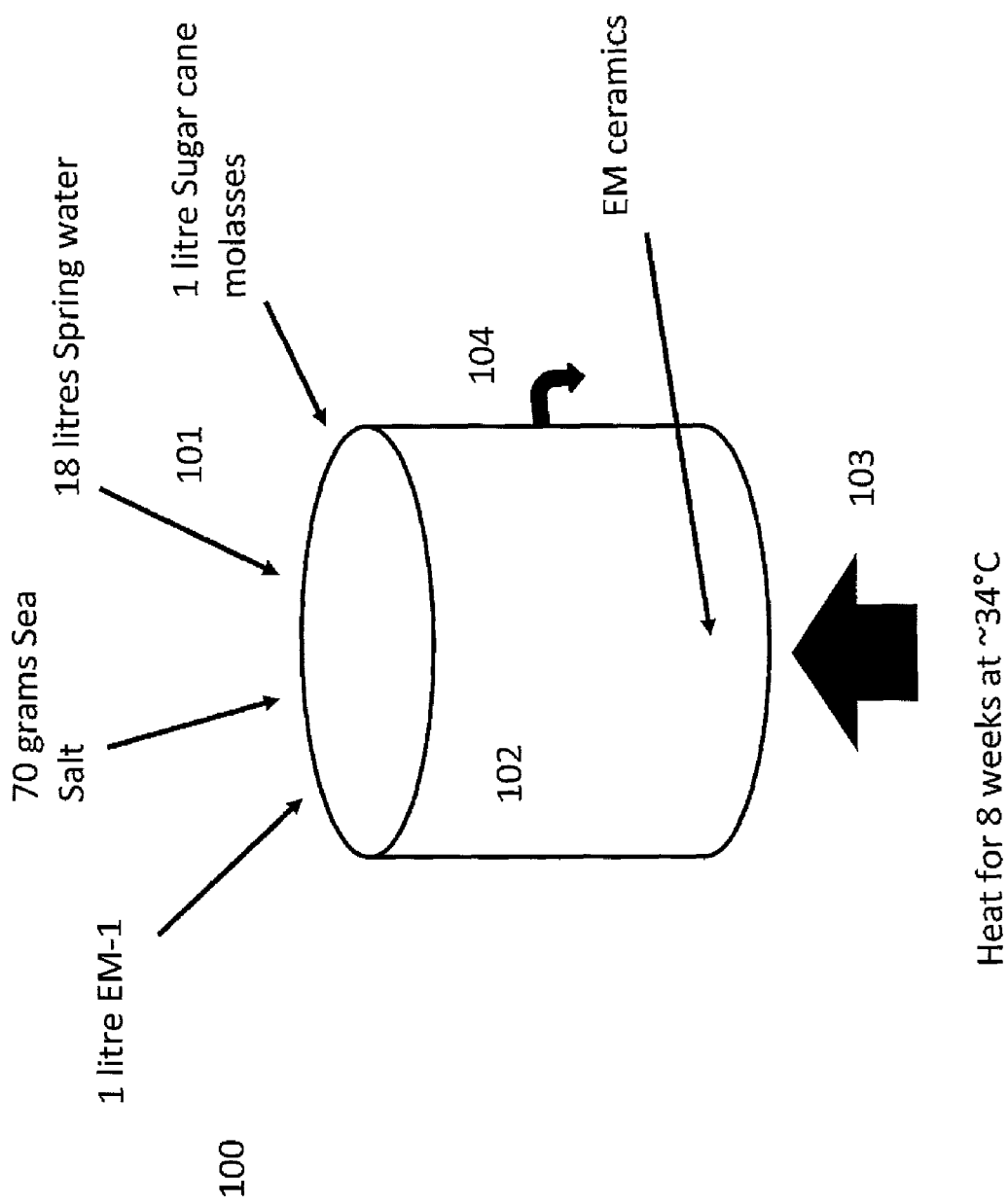

CLEANING FLUID COMPRISING GLYCERIN AND A CULTURE OF MICROORGANISMS

BACKGROUND

Effective Micro-Organisms®, also known as EM Technology® is a trademarked term now commonly used to describe a proprietary blend of different types of predominantly anaerobic organisms. These Micro-organisms co-exist and have beneficial effects in some environments. Typically EM® includes:

Lactic acid bacteria
Photosynthetic bacteria
Actinomycetes
Yeast
Fermenting fungi EM® technology was developed in the early 1980's by Dr. Teruo Higa, a professor at the University of the Ryukyus in Okinawa, Japan, as an alternative to conventional agricultural chemicals. EM® have been marketed since 1983 in Japan. When in contact with organic matter, Effective Micro-Organisms® secrete a number of beneficial substances including vitamins, organic acids, chelated minerals and antioxidants.

Effective Micro-Organisms® has been used in a wide variety of applications, including recycling, and in agriculture and horticulture. It is able to turn food and other kitchen waste into valuable organic material and increases productivity and reduces disease in agriculture and horticulture. It can also provide a solution to certain environmental problems, such as water, air and soil pollution.

EM® works in a number of different ways, firstly by the competitive exclusion of other, harmful Micro-organisms, through the promotion of rapid decomposition of organic matter, accelerating the rupture of compounds such as proteins, sugars, fats and fibres, and in the production of beneficial by-products, such as enzymes, organic acids, amino acids, hormones and antioxidants that promote the health of the environment. EM® comprises facultative anaerobic organisms, meaning that the microbes in question make Adenosine triphosphate (ATP) by respiration in the presence of oxygen, but is also capable of fermentation in anaerobic conditions. In contrast, obligate anaerobes die in the presence of oxygen. This facultative quality of EM® allows it to extend its benefits to aerobic and anaerobic environments.

It is known to use Effective Micro-Organism® as a highly efficient cleaning product. It can be used for the same tasks as a conventional detergents. It has the advantages of being harmless, or even beneficial to health, does not foam up like traditional detergents, meaning that rinsing is often unnecessary, and the microbes in EM® stop mould, fungus and harmful bacteria from growing.

EM® is typically available in concentrated form, such as EM-1® solution. The concentrate form of EM-1® is useful for adding to water for washing vegetables, pouring down sink drains to reduce odours and may also be used in appliances such as washing machines. For general purpose cleaning, however, it needs to be in dilute form.

Typically, EM® is activated from an EM® "mother culture". Typically around 40 ml of EM® is placed in a liter of de-chlorinated water, with 40 ml of molasses. It is typically recommended to use tap water which has been left to sit for 24 hours to allow evaporation of chlorine.

The activation process then involves the heating of the mixture, for example at a temperature typically of 35° C. to 43° C. for at least two weeks. It is possible to use lower temperatures, if longer heating is applied.

Apart from the inconvenience of the process, there are a number of other problems with the resultant cleaning solution. Firstly, once activated, it has a very short "shelf" life. Whereas pre-activation EM® mother culture may last up to 2 years, the activated product often only lasts one to two months. A second problem lies in the texture of the resulting solution, which tends to be rough and abrasive to use and which results in difficulties when cleaning surfaces.

While it is known to combine Effective Micro-Organisms® with detergents, as for example disclosed in US 2007/0190625, it is the prevailing view that Effective Micro-Organisms® is a living culture and that the addition of other chemicals will have a detrimental effect on the culture.

Since EM® is a highly effective and environmentally friendly cleaning agent, it would be useful to overcome these problems and find an EM® based cleaning fluid which is ready diluted, with long shelf life and a texture suitable for easy cleaning.

SUMMARY OF THE INVENTION

In its broadest sense, the invention provides a cleaning fluid, comprising a micro-organism culture and glycerin, wherein the micro-organism culture comprises lactic acid bacteria, actinomycetes, photosynthetic bacteria, yeast and fungi. Preferably the cleaning fluid uses Effective Micro-Organisms® combined with glycerin to produce a more effective cleaning product than effective micro-organisms on its own.

Preferably salt is used in combination with the micro-organism culture and glycerin. More preferably, the salt is free from anti-caking agent. Still more preferably, the salt concentration is substantially 70 grams in 20 liters of cleaning fluid.

The invention also provides a method of producing the cleaning fluid, comprising the steps of diluting the micro-organism culture with water, adding glycerin and heating for a period of time.

Preferably the water is free from fluorides and chlorine. More preferably, the water has been filtered through rock prior to use in the method. Preferably the rock used for filtering is basalt rock. Still more preferably, the water is Highland Spring® water.

Preferably the heating is at a temperature between 21° C. and 43° C. More preferably, the heating is at a temperature of 34° C.

Preferably the time period is at least 8 weeks.

Optionally, EM® ceramics are used to increase the numbers of microbes during the activation process.

The above and other aspects of the present invention will now be described by way of example only with the aid of the accompanying drawing in which:

FIG. 1 shows the apparatus used with the ingredients required according to an embodiment of the invention.

DETAILED DESCRIPTION

In a first embodiment of the invention, a micro-organism culture known as "Effective Micro-Organisms®" or EM-1® is used. This culture comprises lactic acid bacteria, actinomycetes, photosynthetic bacteria, yeast and fungi.

Effective Micro-Organisms® is a multi-culture of coexisting anaerobic and aerobic beneficial Micro-organisms that has a reviving action on humans, animals, and the natural environment. The main species involved in EM® include:

Lactic acid bacteria—*Lactobacillus plantarum, Lactobacillus casei: Lactobacillus lactis*

Photosynthetic bacteria—*Rhodopseudomonas palustris, Rhodobacter sphaeroides*
Yeasts—*Saccharomyces cerevisiae, Candida utilis*
Actinomycetes—*Streptomyces griseus, Streptomyces albus*
Fermenting fungi—*Aspergillus oryzae, Mucor hiemalis*
Lactic Acid Bacteria

*Lactobacillus casei* is a species of genus *Lactobacillus* found in the human intestine and mouth. It is a lactic acid producer and is known to assist in the propagation of desirable bacteria. *Lactobacillus casei* can tolerate a wide range of pH and temperature. It complements the growth of *Lactobacillus acidophilus*, a bacterium which produces the carbohydrate-digesting enzyme amylase. It is documented that it improves digestion and reduces lactose intolerance and constipation.

*Lactobacillus plantarum* is lactic and acetic acid producing member of the genus *Lactobacillus*. It is very widespread, being found in many fermented food products, in saliva and in the anaerobic conditions of ensilage. It is a very flexible and versatile species, with the unusual property that it can respire oxygen, but has no respiratory chain, with the result that the oxygen consumed ends up as hydrogen peroxide. The hydrogen peroxide is believed to be used by the species as an additional means of competing against other microbes.

*Lactococcus lactis* is a Gram-positive, lactic acid producing member of the *Lactococcus* genus. *Lactobacillus lactis* cells are cocci that group in pairs and short chains, and, depending on growth conditions, appear ovoid with typically 0.5-1.5 μm in length. Due to its ability to produce lactic acid, *Lactobacillus lactis* is one of the most important Micro-organisms in the dairy industry and is used in the production of buttermilk and cheese. *Lactobacillus lactis* is also famous as the first genetically modified organism to be used alive for the treatment of human disease.

Photosynthetic Bacteria

*Rhodopseudomonas palustris* is a gram-negative (this relates to characteristics of the cell wall) purple (capable of photosynthesis) non-sulphur (they do not produce sulphur as a byproduct of their photosynthesis) bacterium. It has the unusual and useful property in that it is capable of switching between four different modes of metabolism; photoautotrophic (they can fix carbon using photosynthesis), photoheterotrophic (they use photosynthesis, but obtain organic compounds from elsewhere), chemoheterotrophic (they obtain energy from chemical reactions in their environment, taking organic compounds from their environment) and chemoautotrophic (obtaining energy from chemical reactions, and producing their own organic molecules). Consequently, this species can grow with or without oxygen. It can use light, inorganic compounds, or organic compounds for energy. It can acquire carbon from either carbon dioxide fixation or green plant-derived compounds, and it can also fix nitrogen. This metabolic versatility makes this bacterium potentially suitable for use in biotechnological applications. It has been found to grow in swine waste lagoons, earthworm droppings, marine coastal sediments and pond water.

*Rhodobacter sphaeroides* is a another type of photosynthesizing, purple bacterium. Conditions for its optimum growth are anaerobic phototrophy (both autotrophic and heterotrophic) or, in the absence of light, aerobic chemoheterotrophy. It is also able to fix nitrogen.

Yeasts

*Saccharomyces cerevisiae* is a species of yeast, known alternatively as bakers' yeast and brewers' yeast, due to its use since ancient times in both baking and brewing. It is widely regarded as the most useful type of yeast and as a consequence is one of the most intensely studied eukaryotic organisms in molecular and cell biology. Its cells are round to ovoid, 5-10 micrometers in diameter and it reproduces by a process of division known as budding.

*Candida utilis*, also known as Torula, is a species of yeast, widely used as a flavouring in foods, particularly pet food. It is produced from wood sugars, as a byproduct of paper production.

Actinomycetes

Actinobacteria include some of the most common life, in soil and in both fresh and marine water. They play an important role in the decomposition of organic matter, including cellulose and chitin. This is a vital part of the carbon cycle, allowing the turnover of organic matter, replenishing the supply of nutrients in the soil and is an important part of humus formation.

*Streptomyces griseus* is a gram-positive bacterium of the genus *Streptomyces*. It is commonly found in soil, but has also been found in deep sea sediments, They are producers of antibiotics and other commercially useful secondary metabolites. It has also been demonstrated to be useful in the field of water purification, for example it has been shown in recent tests to be able to reduce the levels of copper nitrate and arsenic in water from dangerously toxic levels. This is achieved by the attraction of the positively charged contaminants to the negatively charged cell walls of the *Streptomyces griseus* followed by mucopolysaccharides bonding the two together.

*Streptomyces albus* is another species of the genus *Streptomyces*, which produces actinomycetin. It is commonly found in dust, soil, grains, and straw.

Fermenting Fungi

*Aspergillus oryzae* is a filamentous fungus, extensively used in oriental cooking. It is used to ferment soybeans, produce rice vinegars and to saccharify rice, potatoes and other grains in the process of making alcoholic drinks such as huangjiu, sake, and shōchū.

*Mucor* is a microbial genus of about 3000 species of moulds commonly found in soil, digestive systems, plant surfaces, and rotten vegetable matter.

The person skilled in the art will appreciate that the exact compositions of Effective Micro-Organisms® varies considerably and that the invention is not limited to any one composition of species of microorganism or ratio of numbers of microorganism. In a preferred embodiment of the invention, EM1® solution, available commercially from Effective Micro-organisms UK, is used as the basis of the culture. It will be appreciated by the person skilled in the art that other Effective Microorganism® or similar microorganism compositions may be used and the invention is not limited to any one type of culture.

Effective micro-organisms is known for its cleaning properties and has been proposed and used as a cleaning agent (see for example http://www.effectivemicroorganisms.co.uk/cleaning.html). Importantly, it has previously been used on its own as a cleaning agent and in combination with soaps and detergents (US 2007/0190625), with the prevailing view in the art that being that since Effective Micro-Organisms® is a culture of living organisms, adding other chemical agents to it would result in the deaths of the organisms and the consequent destruction of the effectiveness of the culture. A key aspect of this invention is the discovery that Effective Micro-Organisms® can be combined with small amounts glycerin to produce an improved cleaning agent, whilst maintaining the benefits of a substantially pure Effective Microorganisms® culture.

The addition of glycerin changes the tactile characteristics of the end product, making it easier to work with. The optimum amount of glycerin to add to the EM® is 1.5 ml per 20 liters of cleaning solution, although up to 5 ml per 20 liters of cleaning fluid may be used and is likely to be effective. Above this amount, if the solution is used on glass or other similar surface, then smearing is likely to result. It will be clear to the person skilled in the art however, that different concentration may be used, for example higher concentrations may be beneficial in certain cleaning applications, while lower concentrations may still be used, although such use is likely to lead to less beneficial results.

A method of producing a cleaning fluid according to the present invention will now be described with reference to FIG. 1. FIG. 1 shows the quantities of ingredients for making 20 liters of the cleaning fluid, although it would be clear to the person skilled in the art that the amounts may be varied proportionately to produce differing output volumes. FIG. 1 shows the apparatus 100 and the material contents 101 needed to produce the cleaning fluids. The apparatus 100 comprises a sealable air tight drum 102. The sealable drum is preferably provided with an adjustable, thermostatically controlled heat source 103. A tap 104 is available to drain off the cleaning fluid.

In an embodiment, Effective Micro-Organisms® ceramic pipes are laid in the base of the drum. EM® ceramics are essentially microbes from EM® solution embedded into clay. Typically, Montmorillonite clay is used. Montmorillonite is a very soft phyllosilicate group of minerals that typically form in microscopic crystals, forming a clay.

EM® Ceramics are formed when montmorillonite clays are fermented with Effective Micro-organisms and then baked at temperatures ranging from 600 to 1200 degrees Celsius. Many of the microbes which make up EM® are able to survive the firing of the clay, after which they are able to multiply within the matrix of the baked clay, given sufficient food to do so. Newly formed organisms can then move out of the clay, to perform their natural functions, feasting on organic matter and harmful microbes. Although Montmorillonite ceramics are conventionally used in EM® ceramics, the invention is not limited to this type of clay. The person skilled in the art would appreciate that alternative clays may also be suitable.

EM® Ceramics are typically used for keeping stored water clear and drinkable. They will prevent calcification of the elements in dishwashers and washing machines. They make water softer and reduce the need for dishwashing and clothes washing detergent. EM's® are natural antioxidants and help to prevent rust in appliances. EM® Ceramics will improve water quality and suppress algae in aquaculture, ponds and dams. They can also be used in swimming pools instead of chlorine. EM® ceramics are available as "Pipes", Rings or as powder. EM® ceramics are typically used at the ratio of 1 Kg per 1000 Liters of water. The "pipes" are tubes, typically around 35 mm in length, which provide a high surface area, improving their efficiency.

Optimally, at least 2 pipes are used with water to produce each liter of cleaning fluid. Preferably, approximately 30 pipes are used for 20 liters of cleaning fluid. However, the person skilled in the art will appreciate that different amounts of EM® ceramic can be used, with a trade-off between cost and effectiveness of the activated solution. Alternatively, in another embodiment, Effective Micro-Organisms® ceramic powder is used. In yet another embodiment, Effective Micro-organisms ceramic rings are used.

EM® activation is not an exact science, and failures can and do occur. To increase the probability that a given culture will develop as required, the quality of the water is of crucial importance. It is known that water used for EM® activation must be chlorine and fluoride free. However, once this precaution has been adhered to, conventional wisdom holds that tap water is adequate for use in EM® activation and dilution. It has been found however that the use of Highland Spring® water, from soil free from pesticides and pollutants, results in a higher level of microbe reproduction than tap water. The maximum time for which a sample produced with tap water was effective has been found to be four weeks, once diluted. Using Highland Spring® water, this "shelf-life" has been demonstrated to be extended to up to six months. Hence in an embodiment of the invention, spring water is used for the activation and dilution of the cleaning fluid culture. The characteristics of Highland Spring® water is that it is rainwater which has been filtered naturally through basalt rock. Typically the filtration period is around 15 years. However, it will be appreciated by the person skilled in the art that wide variations in the time taken for filtration can occur without detrimental consequences for the quality of the water produced. It will also be appreciated that different types of permeable rocks may be used. It will also appreciated by the person skilled in the art that other forms of pollutant and pesticide free water, such as distilled water, may be equally effective. It would also be clear to the person skilled in the art that the use of spring water would improve the activation process of EM® cultures used without the glycerin.

Salt is used in the cleaning fluid as a method of preservation. It has been found that the use of sea salt, without any anti-caking agents, provide for a good environment for the microbes to reproduce. The salt level is a tradeoff between the preservation of the solution and the health of the microbes. Excess salt will of course, kill the microbes. It has been found that an optimal level is 70 g of salt per 20 liters of solution, although higher levels of salt are possible. In an embodiment of the invention therefore, 70 g of salt is used in every 20 liters of cleaning fluid. The person skilled in the art will appreciate that the level of salt may be varied.

In order to provide nutrition for the developing microbial culture, sugar cane molasses is added to the drum. Preferably, for the sake of purity and health of the microbes, molasses produced by organic farming techniques is preferred. Preferably, sugar cane molasses is used. The person skilled in the art will appreciate that other foods may be used for the microbes and that the invention is not limited to any one way of provided nutrition for the growth of the microorganism culture.

In an embodiment of the invention 20 liters of the cleaning fluid may be produced using 18 liters of water, 1 liter of molasses and a liter of the microorganism culture described above, hereafter referred to as EM-1® Preferably, 70 g of salt, 1.5 ml of glycerin in 30 EM® ceramic pipes are added. Preferably, to ensure purity and the health of the microbial culture, glycerin producing by organic farming techniques is used. However, the invention is not limited to any given production technique for the ingredients. The proportions of these ingredients may be varied, as would be appreciated by the person skilled in the art and the invention is not limited to any set proportion of amount of ingredients.

The mixture is then sealed in the drum and heated. Periodic release of gases is required. Preferably the mixture is heated at 34° C. However, the temperature may be any in a range from 20° C. to 43° C. There is a trade-off between temperature and the length of time for which the culture is heated. A higher temperature will allow a shorter period of fermentation. The length of heating is a minimum of two weeks. Preferably the period is in the order of six to eight weeks. In a preferred embodiment of the invention, the culture is heated for two months at 34° C. The person skilled in the art will appreciate that variations in the temperature and length of fermentation can be varied and that the invention is not limited to any specific conditions.

Preferably, according to an embodiment, after heating, the culture is further diluted. Preferably, 10 ml of culture is used with 990 ml of water. In a preferred embodiment of the invention, the water is Highland Spring® water. However, the person skilled in the art will appreciate that different concentrations may be appropriate for different purposes and the invention is not limited by any specific concentration. Furthermore, the person skilled in the art will appreciate that the use of different types of water may be used and that the invention is not limited to a particular type or quality of water.

The invention claimed is:

1. A cleaning fluid comprising glycerin and a culture of micro-organisms, said culture comprising lactic acid bacteria, actinomycetes, photosynthetic bacteria, yeast and fungi.

2. A cleaning fluid as claimed in claim 1 further comprising salt.

3. A cleaning fluid as claimed in claim 2 wherein the salt is free from anti-caking agent.

4. A cleaning fluid as claimed in claim 2 wherein the salt concentration is substantially 70 grams in 20 liters of cleaning fluid.

5. A method of making a cleaning fluid comprising glycerin and a culture of micro-organisms, the culture comprising lactic acid bacteria, actinomycetes, photosynthetic bacteria, yeast and fungi, the method comprising the steps of
    diluting the micro-organism culture with water;
    providing food for said micro-organism culture;
    adding glycerin;
    heating the culture at a temperature for a period of time.

6. A method of making a cleaning fluid as claimed in claim 5, wherein the water is free from fluorides and chlorine.

7. A method of making a cleaning fluid as claimed in claim 5, wherein the water has been filtered through rock.

8. A method of making a cleaning fluid as claimed in claim 7, wherein the rock is basalt rock.

9. A method of making a cleaning fluid as claimed in claim 5, wherein the microorganism culture, water, food for the micro-organism culture, and glycerin are placed and heated in a sealed drum.

10. A method of making a cleaning fluid as claimed in claim 9 further comprising placing ceramics impregnated with a micro-organism culture into the sealed drum.

11. A method of making a cleaning fluid as claimed in claim 10, wherein the ceramic is in the form of tubes.

12. A method of making a cleaning fluid as claimed in claim 10, wherein the ceramic is in the form of rings.

13. A method of making a cleaning fluid as claimed in claim 10, wherein the ceramic is in the form of powder.

14. A method of making a cleaning fluid as claimed in claim 5, wherein the period of time is at least two weeks.

15. A method of making a cleaning fluid as claimed in claim 5, wherein the temperature is at least 21° C.

16. A method of making a cleaning fluid as claimed in claim 5, wherein the temperature is less than 43° C.

17. A method of making a cleaning fluid as claimed in claim 5, wherein the temperature is in the range of 32° C. to 36° C.

18. A method of making a cleaning fluid as claimed in claim 5, wherein the period of time is at least eight weeks.

19. A method of making a cleaning fluid as claimed in claim 5, wherein the food for the micro-organism culture includes molasses.

* * * * *